(12) United States Patent
Ohman et al.

(10) Patent No.: US 7,564,045 B2
(45) Date of Patent: Jul. 21, 2009

(54) OPTICAL ASSAY SYSTEM

(75) Inventors: Per Ove Ohman, Uppsala (SE); Tomas Lindstrom, Uppsala (SE); Ib Mendel-Hartvig, Uppsala (SE)

(73) Assignee: AMIC AB, Uppsala (SE)

( * ) Notice: Subject to any disclaimer, the term of this patent is extended or adjusted under 35 U.S.C. 154(b) by 125 days.

(21) Appl. No.: 11/454,993

(22) Filed: Jun. 15, 2006

(65) Prior Publication Data

US 2006/0289787 A1    Dec. 28, 2006

(30) Foreign Application Priority Data

Jun. 17, 2005    (SE)    .................................... 0501397

(51) Int. Cl.
*G01N 21/64*    (2006.01)
(52) U.S. Cl. ................. 250/458.1; 422/82.08
(58) Field of Classification Search .............. 422/82.08; 250/458.1
See application file for complete search history.

(56) References Cited

U.S. PATENT DOCUMENTS

| | | | |
|---|---|---|---|
| 4,789,628 A * | 12/1988 | Nayak ........................ | 435/7.94 |
| 5,458,852 A | 10/1995 | Buechler | |
| 5,779,978 A * | 7/1998 | Hartmann et al. ........ | 422/82.05 |
| 5,885,527 A | 3/1999 | Buechler | |
| 5,922,615 A | 7/1999 | Nowakowski et al. | |
| 6,019,944 A | 2/2000 | Buechler | |
| 6,074,616 A | 6/2000 | Buechler et al. | |
| 6,106,779 A | 8/2000 | Buechler et al. | |
| 6,113,855 A | 9/2000 | Buechler | |
| 6,143,576 A | 11/2000 | Buechler | |
| 6,156,270 A | 12/2000 | Buechler | |
| 6,194,222 B1 | 2/2001 | Buechler et al. | |
| 6,271,040 B1 | 8/2001 | Buechler | |
| 6,297,060 B1 | 10/2001 | Nowakowski et al. | |
| 6,302,919 B1 | 10/2001 | Chambers et al. | |
| 6,317,206 B1 * | 11/2001 | Wulf .......................... | 356/317 |
| 6,391,265 B1 | 5/2002 | Buechler et al. | |
| 6,392,894 B1 | 5/2002 | Buechler et al. | |
| 6,669,907 B1 | 12/2003 | Buechler | |
| 6,767,510 B1 | 7/2004 | Buechler | |
| 6,830,731 B1 | 12/2004 | Buechler et al. | |
| 6,905,882 B2 | 6/2005 | Buechler | |

(Continued)

FOREIGN PATENT DOCUMENTS

WO    WO-2004/104585 A1    12/2004

OTHER PUBLICATIONS

U.S. Appl. No. 09/613,650, filed Jul. 11, 2000 for Buechler.

(Continued)

*Primary Examiner*—Constantine Hannaher
(74) *Attorney, Agent, or Firm*—Morrison & Foerster LLP

(57) ABSTRACT

An optical reader for an optical assay arrangement including a polymeric sample substrate having a reaction-site surface provided with protruding microstructures and at least one reaction-site area; a light source for illuminating the reaction-site area; and a detector device for detecting light emitted from the reaction-site area. The light source is arranged to inject exciting light rays into the polymeric sample substrate with a controlled angle of incidence such that the protruding microstructures guide the exciting light rays in the direction of the reaction-site area, and the detector device detects light emitted from the at least one reaction-site area.

30 Claims, 10 Drawing Sheets

U.S. PATENT DOCUMENTS

| | | |
|---|---|---|
| 7,195,872 B2 * | 3/2007 | Agrawal et al. ............ 435/6 |
| 7,416,700 B2 | 8/2008 | Buechler et al. |
| 2003/0035758 A1 | 2/2003 | Buechler et al. |
| 2003/0086031 A1 | 5/2003 | Taniguchi et al. |
| 2004/0024107 A1 | 2/2004 | Nojiri et al. |
| 2004/0077103 A1 | 4/2004 | Buechler |
| 2004/0209392 A1 | 10/2004 | Craighead et al |
| 2005/0049325 A1 | 3/2005 | Chisholm et al. |
| 2005/0112782 A1 | 5/2005 | Buechler |
| 2005/0136552 A1 | 6/2005 | Buechler |
| 2005/0147531 A1 | 7/2005 | Buechler |
| 2007/0154970 A1 | 7/2007 | Buehcler et al. |

OTHER PUBLICATIONS

U.S. Appl. No. 09/712,615, filed Nov. 13, 2000 for Buehcler et al.

* cited by examiner

OPTICAL ASSAY SYSTEM

CROSS-REFERENCE TO RELATED APPLICATION

This application is a Utility application claiming priority to Swedish Application Ser. No. SE 0501397-4, filed Jun. 17, 2005, which is hereby incorporated by reference in its entirety

TECHNICAL FIELD OF THE INVENTION

The present invention relates to an improved optical reader for an optical assay arrangement comprising a polymeric sample substrate provided with protruding microstructures, e.g. micropillars. The invention also relates to a polymeric sample substrate provided with protruding microstructures, and an optical assay arrangement comprising an optical reader and a polymeric sample substrate according to this invention.

BACKGROUND OF THE INVENTION

Analytical and diagnostic determinations can be performed on liquid samples by means of optical assays based on the detection of analytes in a sample, such as e.g. polynucleotide analytes, receptor proteins or antiligand molecules. One important application of optical assays is the field of immunology, in which the analyte is detected with the aid of a specific antibody, which is capable of binding to the analyte to form optically detectable complexes, e.g. by labeling the analyte with a fluorophore, or by providing a fluorophore-labeled conjugate before the optical detection. The detection may be performed by means of an optical reader, which is capable of illuminating the assay support substrate with an exciting light source and of detecting the fluorescent light emitted from the fluorophores.

An optical assay is performed by an optical assay arrangement comprising a sample supporting substrate and an optical reader. The optical reader comprises a source and detector for electromagnetic radiation within the optical wavelength region (i.e. between approximately 40 nm and 1 mm), and suitable optical waveguiding means for focusing and filtering. The sample support comprises a substrate of e.g. a polymeric material provided with one or more reaction site areas, comprising spots or lines of probe molecules, e.g. of an antibody, providing binding sites for molecules of the analyte, i.e. the target molecules, that may be present in a sample. When the sample is brought in contact with the probe molecules on the support surface, the target molecules in the sample will react with the probe molecules on the surface of the substrate and form optically detectable spots or lines. Luminescent light will be emitted when the substrate is illuminated with the exciting light source of the optical reader, thereby indicating that a reaction has occurred between the target molecules of the sample and the probe molecules of the reaction sites.

Luminescent light is emitted either as fluorescent light or phosphorescent light, or as chemiluminescent light. Fluorescence and phosphorescence may be defined as the emission of electromagnetic radiation resulting from absorbed exciting electromagnetic radiation, the fluorescent light lasting less than $1 \times 10^{-8}$ s after the excitation, and phosphorescent light lasting longer, i.e. is decaying more slowly after the exposure to the exciting light, while chemiluminiscence is the emission of light resulting from a chemical reaction.

In fluorescence (and phosphorescence), the exciting radiation normally has a shorter wavelength (i.e. higher energy) than the emitted radiation, although the reverse may be true for multi-photon fluorescence. The fluorescent behaviour may be studied in a steady state or time-resolved, and fluorescence spectroscopy involves e.g. single- and multi-photon fluorescence, FRET (fluorescence resonance energy transfer), and fluorescence up-conversion. In fluorescence assays, the wavelength of the exciting and the emitted radiation depends on the type of fluorophore, which may be of an organic or inorganic origin, e.g. cyanine dyes or nanocrystals. As an example, the common fluorophore Cy5 is typically excited with 649 nm, and the emitted light is measured at 670 nm.

In optical assays, the concentration of an analyte in the sample may be determined by measuring the intensity of emitted fluorescent or phosphorescent light, by means of the light detector of an optical reader, thereby enabling quantitative measurements. Consequently, the efficiency of the illumination of a reaction site area with exciting light, as well as the efficiency of the collection of the emitted light, will have an effect on he performance of the optical assay.

Further, the reaction sites on a substrate surface may be provided with an array of spots or lines of different probe molecules, binding different target molecules. Therefore, an optical reader may be designed to be capable of determining the presence of several analytes in a sample, by means of different fluorophores.

A scanning optical reader is a conventional optical reading device for illuminating detection sites on a substrate and for detecting the emitted light. The scanning optical reader preferably comprises a narrowband exciting light source, such as a laser, and the laser light is focused on each individual detection site. The emitted light from each detection site is focused on an optical detector, such as a photodiode or a PMT (photomultiplier tube). In a scanning optical reader, the entire surface of the support substrate is scanned by a relative X-Y-movement between the optical means and support. The focusing means of a scanning optical reader may e.g. comprise confocal optics only collecting emitted light in the depth of focus of the objective lens, e.g. by blocking unwanted light by a pinhole and thereby reducing the detected noise.

An imaging optical reader is another conventional optical reading device, which is capable of detecting a two-dimensional array of pixels. The imaging optical reader comprises an exciting light source, e.g. a xenon lamp, for illuminating a large part of the surface area (or the entire surface area) of the substrate, and a detector capable of detecting emitted light from the entire detection site-area simultaneously, e.g. a CCD (Charged-Coupled Device)-imager, which utilizes MOS (Metal-On-Semiconductor)-technology, and offers a high quantum efficiency, sensitivity and spatial resolution. Further, a wideband light source may be provided with wavelength filters to provide monochromatic radiation.

A prior art sample supporting substrate for liquid samples is disclosed in WO 03/103835, said substrate being microstructured to form a capillary flow path for the sample, forming a pattern of micropillars protruding from the surface of the substrate. The size of the micropillars is in the micrometer-range, 1 micrometer $(\mu m)=1\times 10^{-6}$ m, and the spacing is adapted to induce capillary action of the liquid. In an optical assay arrangement comprising a sample supporting substrate provided with micropillars, the light paths of both the exciting light and the emitted light will be affected by the micropillars, thereby influencing the performance of the optical assay arrangement. The optical properties of the material of the substrate, such as the light transmission, will also affect the optical assay performance.

A prior art optical reader is described in WO 01/575501, which discloses optical imaging of a sample on a transparent substrate, without any protruding microstructures. The optical reader comprises an exciting energy source to stimulate emission of detectable light from the sample, and the substrate is provided with a reflective surface located below the sample to reflect the emitted light into the detection means.

Further, a prior art optical assay arrangement is disclosed in WO 2004/104585, which relates to a microstructured microarray support, in which the height of the microstructures is adapted to the depth of focus of the optical arrangement.

It is an object of this invention to provide an optical reader and a polymeric sample substrate suitable for an optical assay arrangement, in order to achieve an improved optical assay performance, by accomplishing an efficient illumination of the reaction site area of the substrate and an efficient collection and detection of the emitted light, as well as a reduction of the detected optical background signal, thereby increasing the resulting signal-to-noise ratio.

DESCRIPTION OF THE INVENTION

These and other objects are achieved by the optical reader, the polymeric sample substrate and the optical assay arrangement according to the appended claims.

The optical reader for an optical assay arrangement comprises a light source for illuminating a polymeric sample substrate having a reaction site-surface comprising at least one reaction site area provided with protruding microstructures. The optical reader further comprises a detector device for detecting light emitted from said at least one reaction site-area. The light source is arranged to inject exciting light rays into the polymeric sample substrate with a controlled angle of incidence selected to cause the optical substrate properties to guide the exciting light rays in the direction of a reaction site-area, the protruding microstructures contributing to said optical substrate properties.

The polymeric substrate may be at least partly covered by an additional layer with selected optical properties, and this layer contributes to the optical substrate properties.

The layer may be applied as an optically wetting layer arranged to increase the angle of refraction of the exciting light rays inside the substrate.

The additional layer may at least partly cover the protruding microstructures and/or the carrier surface of the substrate.

The additional layer may be arranged to absorb selected optical wavelengths, and may consist of a tape of a suitable material attached to the substrate.

The light source may be adapted to illuminate the polymeric sample substrate through a light guiding device arranged to control the refraction angle of the exciting light rays, and the light guiding device may comprise a prism, or a diffractive or refractive grating provided on a surface of the substrate.

Further, the light source may have a position relative the polymeric sample substrate to illuminate the reaction-site surface, a carrier surface, or an edge wall of the polymeric sample substrate.

The optical reader may be arranged to cause the angle of refraction to exceed the critical angle for total internal reflection to occur within the polymeric sample substrate.

The detector device of the optical reader may have a position relative the polymeric sample substrate to collect fluorescent or phosphorescent light emitted from a reaction site-area of a substrate, and the emitted light may be guided in the direction of the detector device by the optical substrate properties.

The detector device may have a position relative the polymeric sample substrate to receive emitted fluorescent or phosphorescent light escaping from the carrier surface or from an edge wall of the substrate.

Further, the light source may have a position relative the polymeric sample substrate to illuminate a first surface or edge wall of the substrate, and the detector device may have a position relative the polymeric sample substrate to receive emitted fluorescent or phosphorescent light escaping from the same first surface or edge wall, or from any other surface or edge wall of the substrate.

The optical reader may be arranged as an imaging optical reader or as a scanning optical reader.

The polymeric sample substrate for an optical assay arrangement has a reaction-site surface comprising at least one reaction site-area provided with protruding microstructures, the substrate at least partly covered with an additional layer having selected optical properties, with a light guiding device attached on a surface for controlling the incidence angle of light rays illuminating the substrate.

The additional layer may at least partly cover the protruding microstructures and/or the carrier surface of the substrate, and may be an optically wetting layer arranged to increase the angle of refraction of the exciting light rays inside the substrate.

Further, said additional layer may be arranged to absorb selected optical wavelengths, and may consist of a tape of a suitable material attached to the substrate.

Said light guiding device may comprise a prism or a diffractive or refractive grating.

Other features and further advantages of the invention will be apparent from the non-limiting embodiments of the invention disclosed in the following description and figures, as well as from the appended claims.

BRIEF DESCRIPTION OF THE DRAWINGS

The present invention will now be described in more detail and with reference the drawings, of which.

DESCRIPTION OF PREFERRED EMBODIMENTS

The terms and expressions used in the description and in the claims are meant to have the meaning normally used by a person skilled in the art.

Additionally, the prefix "micro" is used herein to define a device comprising at least one feature having a length, width or height normally expressed in micrometers (μm, $1\times10^{-6}$ m).

According to this invention, an improved performance, e.g. an increased signal-to-noise ratio, of an optical assay arrangement is achieved by a polymeric substrate provided with protruding microstructures and selected optical substrate properties, and by an optical reader comprising a light source and a detector device, the light source capable of injecting exciting light rays into the substrate with a certain angle of incidence, thereby causing the optical substrate properties to guide the exciting light rays to propagate in the direction of a reaction site-area of the substrate.

Figure 1A:
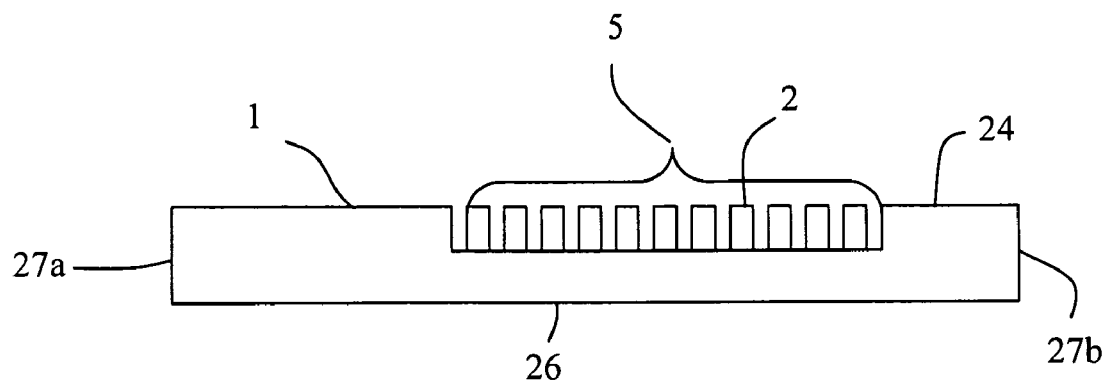
FIG. 1a illustrates a polymeric sample substrate provided with protruding microstructures forming micropillars.

FIG. 1a illustrates schematically a first embodiment of a polymeric sample substrate 1 for an optical assay arrangement, according to this invention, the sample substrate provided with a pattern of protruding microstructures 2, which may be arranged to form a capillary flow path for the sample. The size of the substrate is preferably adapted to form a suitable carrier for one or more reaction site areas 5 for an optical assay, and a prior art microarray slide is rectangular, with a size of 25 mm×75 mm. The thickness of the substrate may be e.g. approximately 1 mm and the width and length e.g. between approximately 1 mm and 100 mm, forming an approximately rectangular or quadratic surface area. The surface of the substrate provided with the reaction sites 5 is hereinafter referred to as the reaction-site surface 24, and the other, opposite surface is hereinafter referred to as the carrier surface 26. Further, the substrate has a number of edge walls, and two edge walls 27a and 27b are indicated in this figure. A rectangularly or quadratically shaped substrate has four straight edge walls, but a polymeric sample substrate according to further embodiments of this invention may, alternatively, have any other suitable shape, as well as e.g. curved edge walls. The material of the substrate is preferably a thermoplastic polymer with suitable optical properties, such as e.g. a cycloolefinpolymer or a cycloolefincopolymer, and the substrate may be manufactured by a polymer replication of a master structure, e.g. by injection molding.

Figure 2A:
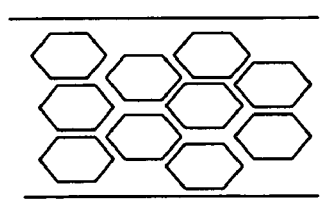
FIG. 2a,b shows exemplary cross sections of micropillars.
Figure 2B:
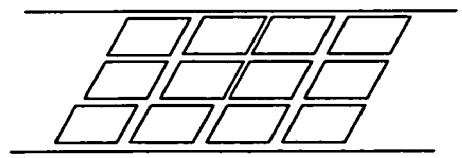

FIG. 2a,b illustrates exemplary cross sections of the protruding microstructures of the support substrate, the microstructures forming micropillars or microposts. The micropillars may have e.g. any of a circular, elliptical, rhombic, triangular, square, rectangular, heptagonal, hexagonal cross section, a combination thereof, or any fraction of these shapes.

The present invention is applicable in optical fluorescence/phosphorescence binding assays, and the protruding microstructures, as well as other optical properties of the substrate material, will influence the performance of the optical assay. The material of the polymeric substrate is preferably selected to obtain certain desirable optical properties, such as a high optical transmittance only in the wavelength ranges of the exciting light and of the emitted light, and high absorbance of other wavelengths, high and temperature-stable refractive index to provide an improved focusing, low haze scattering and low birefringence.

The protruding microstructures of the substrate are contributing to the optical properties of the substrate. The microstructures exhibits optically focusing properties for both the exciting light rays and the emitted fluorescent light. The microstructures are surface enlarging, and will increase the exciting capacity of the substrate due to an increase of the number of photons in the surface coating. When the labels are fluorescent, the emitting capacity of the support is increased due to an increase of the number of photons emitted from the fluorescent dye reaching the optical detection system, and a reduction of the noise is achieved by avoiding unwanted background fluorescence by reducing the number of photons reaching in and/or out of the substrate of the support. Thus, the optical properties of a polymeric substrate provided with protruding microstructures, e.g. micropillars, affects the performance of an optical assay by increasing the signal-to-noise ratio.

The invention relates to an optical reader suitable for an optical assay arrangement comprising the above-described polymeric sample substrate, provided with a pattern of protruding microstructures, e.g. micropillars. The detected signal is increased by the enlargement of the support surface area caused by the micropillars, resulting in more binding sites and, consequently, in a higher fluorescent signal. The micropillars also result in an increased hydrophobic behavior of the surface of the substrate, since the wetting angle is higher for a structured polymer as compared to a planar polymer, facilitating e.g. the printing of high-density microarrays of probe spots. The optical properties of the polymeric substrate is affected by the configuration of the microstructures, such as e.g. by the shape, height, width, thickness and spacing of the micropillars.

Additionally, the polymeric sample substrate may be provided with an additional layer selected to achieve a desired optical behaviour and selected optical properties of the substrate. This layer may be applied on the reaction site surface or on the carrier surface, or on both, and on one or more of the edge walls of the substrate, covering an entire edge wall or surface or only parts of an edge wall or surface, and it may be applied on the protruding microstructures, at least partly covering the microstructures. Furthermore, the additional layer may be of arbitrary shape, and it may be inhomogeneous, consisting of e.g. small particles or pyramids, or homogenous. It may also include a relief structure forming a diffractive or a refractive grating. The material, thickness and homogeneity of this layer is preferably selected to provide a desired reflectivity, transparency or absorption of the exciting light, the emitted light, or of both, and a layer of a material and thickness selected to achieve a high optical absorption will create a "beam dump" for optical radiation. The additional layer may e.g. be applied as a film, a tape, a paint, a fluid, or as a gel, and may comprise an organic or inorganic material, e.g. a metal, a dielectric or a semiconducting material, a polymer or a ceramic, and may further comprise pigments or dyes. Further, the additional layer may be an optically wetting layer, applied with no air between the layer and the surface. If the material of the layer has a refractive index that is larger than the refractive index in air, an increase of the angle of refraction of the exciting light rays can be achieved inside the substrate.

Figure 1B:
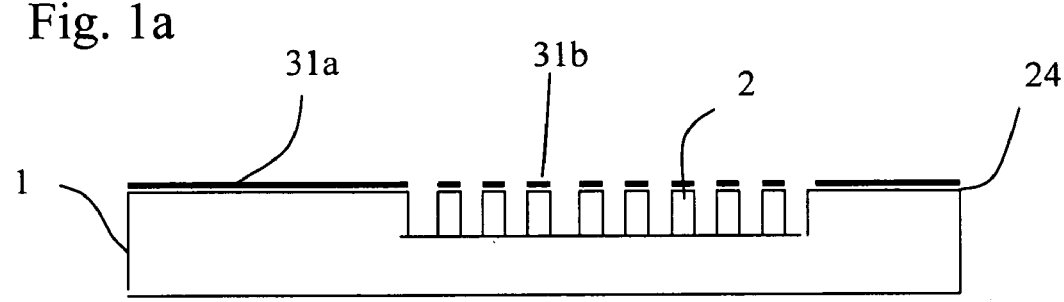
FIG. 1b illustrates a polymeric sample substrate provided micropillars partly covered by an additional layer.

FIG. 1b illustrates a second embodiment of polymeric sample substrate 1 according to this invention, provided with an additional layer 31a,b, as described above, of which a first section 31a of the additional layer covers the entire plane part of the reaction-site surface 24 of the substrate, and a second section 31b covers the top surfaces of the micropillars 2.

However, in order to take advantage of the above-described selected optical properties of a polymeric substrate, the optical reader according to this invention is configured with a light source capable of injecting exciting light rays into the polymeric substrate with a specific angle of incidence, which is selected to cause the optical properties of the polymeric substrate of the optical assay arrangement to guide the light to propagate towards the reaction site-area, thereby resulting in a more efficient illumination of the reaction sites with exciting light, in order to improve the performance of the optical assay.

According to a further embodiment of the optical reader according to this invention, the performance of the optical assay is improved by the detecting device of the optical reader being capable of detecting emitted light guided by optical properties of the polymeric substrate in the direction of the detecting device.

Figure 3:
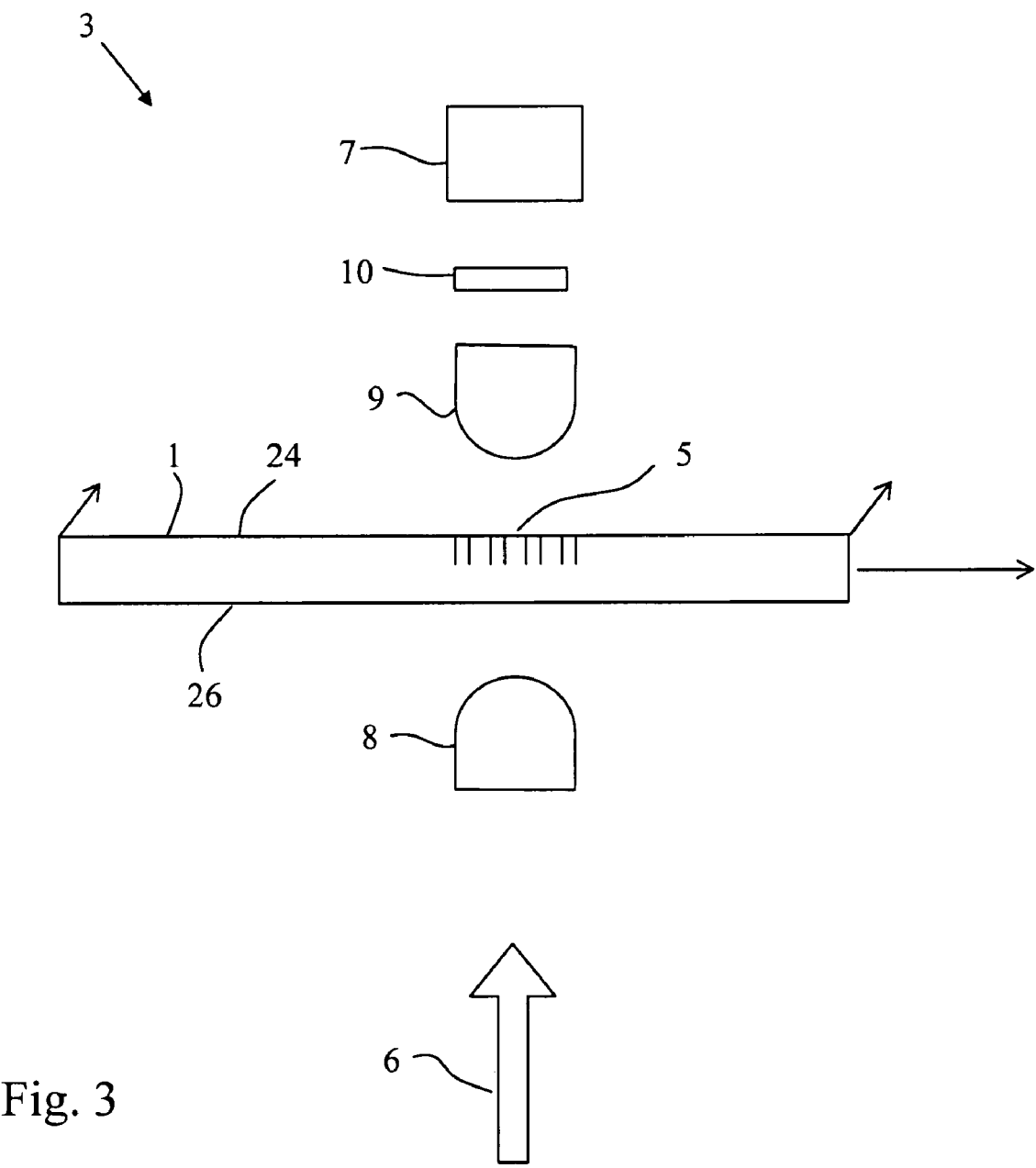
FIG. 3 illustrates an optical assay arrangement comprising a scanning optical reader and a polymeric substrate.

FIG. 3 shows an exemplary set-up of an optical assay arrangement comprising a scanning optical reader 3 and a polymeric sample substrate 1, provided with a microstructured reaction site-area 5. The sample substrate is arranged to be movable relative the optical reader, such that the entire reaction site-area 5 of the sample substrate is scanned. The scanning optical reader comprises an exciting light source 6 positioned to illuminate the carrier surface 26 of the substrate and a detector device 7, e.g. a PMT, positioned to collect light emitted from the reaction-site surface 24 of the substrate. The optical reader further comprises lenses 8 and 9 for focusing the exciting light onto the substrate and for focusing the emitted light onto the detector, and optical filters 10.

Figure 4:
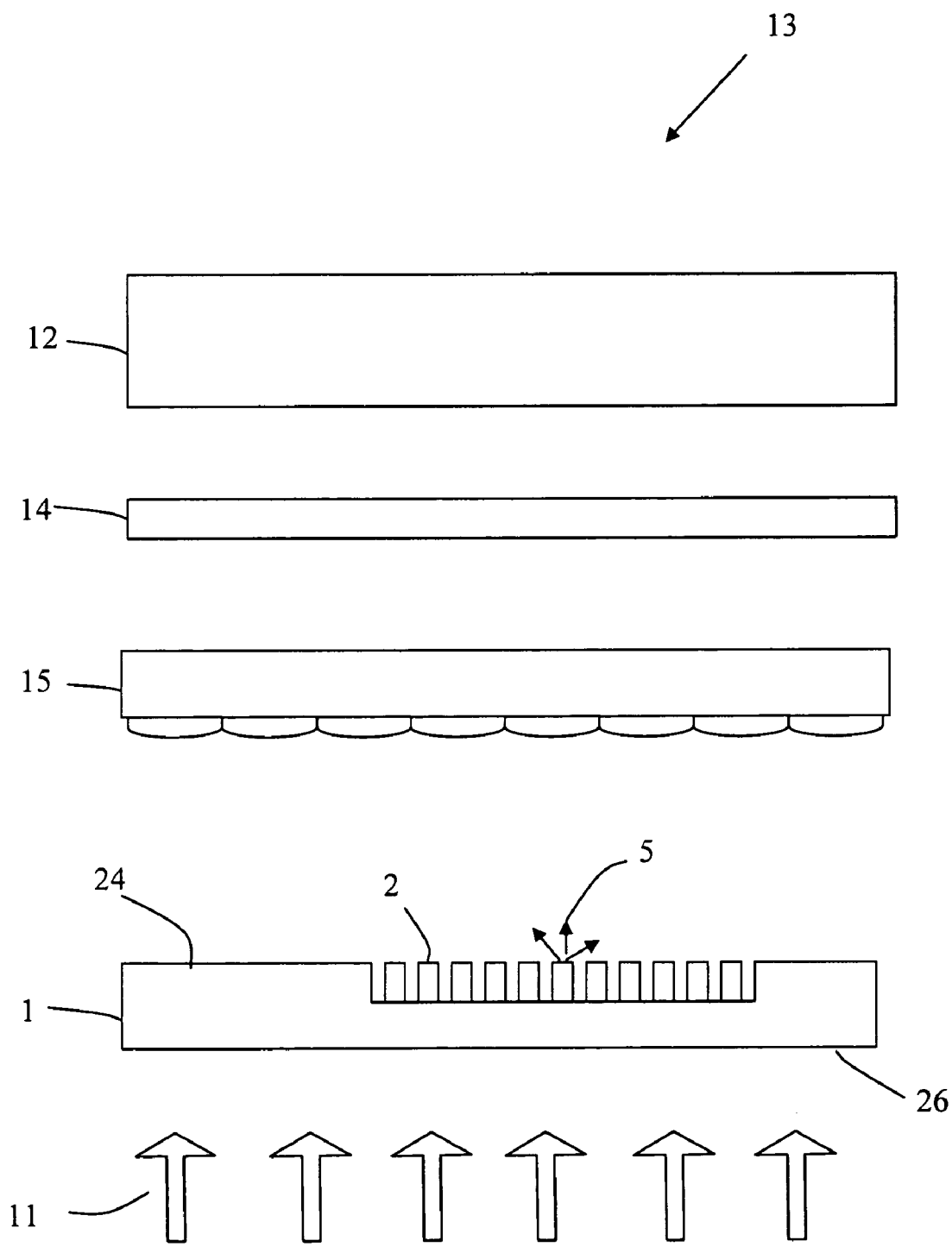
FIG. 4 illustrates an optical assay arrangement comprising an imaging optical reader and a polymeric substrate.

FIG. 4 shows an exemplary set-up of an optical assay arrangement comprising an imaging optical reader 13 and a polymeric sample substrate 1, provided with a reaction site-area 5 having protruding micropillars 2. The imaging optical reader comprises an exciting light source 11 located to illuminate the entire carrier surface 26 of the substrate and a detector device 12, e.g. a CCD, located to detect emitted light from the entire reaction site-area 5 simultaneously. The imaging optical reader is further provided with a lens 13 for collecting and focusing the emitted light onto the detector 12, as well as an optical filter 14.

In order to achieve an improved performance of an optical assay arrangement, the optical reader according to this invention is capable of being positioned in relation to a polymeric sample substrate to inject exciting light rays into said substrate at a controlled angle of incidence selected to cause the optical properties of the substrate to guide the exciting light rays in the direction of the reaction sites.

According to one embodiment of the optical reader, the substrate is illuminated through a light guiding device in order to achieve the desired incidence angle, such as a prism or a grating, to be located on the reaction site surface, on the carrier surface, or on an edge wall of the substrate.

According to a further embodiment of the optical reader according to this invention, the detecting device is capable of being positioned in relation to a polymeric sample substrate to detect emitted light guided by optical properties of said substrate, in the direction of the detecting device.

Figure 5A:
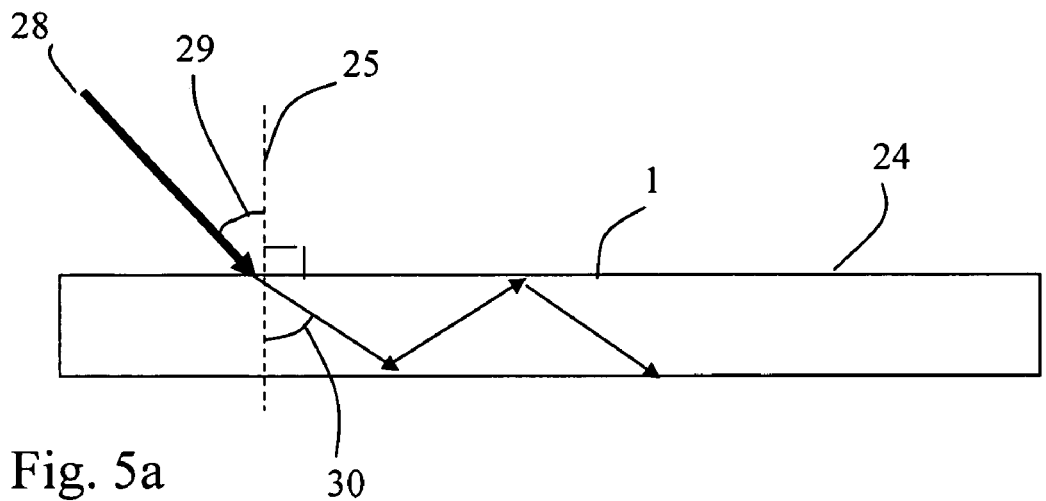
FIG. 5a illustrates the angle of incidence and the angle of refraction of exciting light ray entering a polymeric substrate.

In order to explain a concept of this invention, FIG. 5a illustrates light rays 28 injected into a polymeric sample substrate 1, the light ray 28 forming an angle of incidence 29 with the normal 25 to the substrate surface 24, the incidence angle 29 depending on the position of the light source (not shown in the figure) in relation to the substrate. The injected light ray will be refracted by the polymeric substrate to form an angle of refraction 30 inside the substrate, in relation to the normal 25, depending on the refractive index of the substrate material. When the incidence angle 29 is selected such that the angle of refraction 30 of the refracted light rays inside the substrate coincides with, or exceeds, if allowed by the optical conditions, the critical angle for total internal reflection to occur within the substrate, the exciting light rays will propagate within the substrate by total internal reflection, as indicated by the arrows.

Figure 5B:
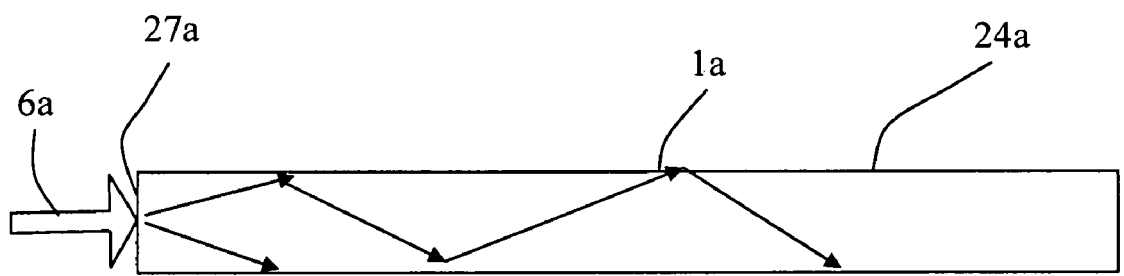
FIG. 5b illustrates exciting light rays entering a polymeric substrate in the vicinity of a substrate edge wall.
Figure 5B:
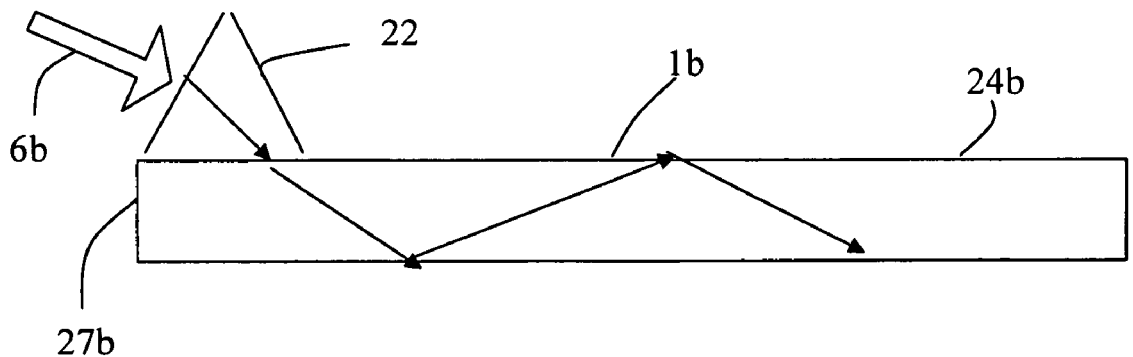

FIG. 5b shows two exemplary configurations to further explain the concept of this invention, by means of the light sources 6a, 6b arranged to inject exciting light rays into a substrate 1a, 1b in the vicinity of an edge wall 27a, 27b of the substrate.

The first light source 6a is positioned to inject light rays directly into an edge wall 27a of the first substrate 1a, and the incidence angle of the light rays causes total internal reflection to of the exciting light rays to occur within the substrate.

The second light source 6b is positioned to inject light rays into the top surface 24b of the second substrate 1b. The light rays are injected in the second substrate 1b at a point near the edge wall 27b of the substrate, through a prism 22, which is placed on the surface 24b in order to control the incidence angle of the light rays, causing total internal reflection of the exciting light rays to occur within the substrate 1b.

The total internal reflection occurring within the substrate 1a and 1b will create an evanescent field at the boundary between the polymeric substrate and air, extending approximately 300-400 nm into air, and capable of an efficient excitement of fluorophores of reaction sites (not shown), that may be provided on the substrate.

However, according to other embodiments of this invention, the angle of incidence is selected not to coincide with or exceed the critical angle for total internal reflection, and the angle of incidence may e.g. be selected to be zero in relation to the normal, i.e. the impinging light rays are parallel to the normal 25.

Figure 6:
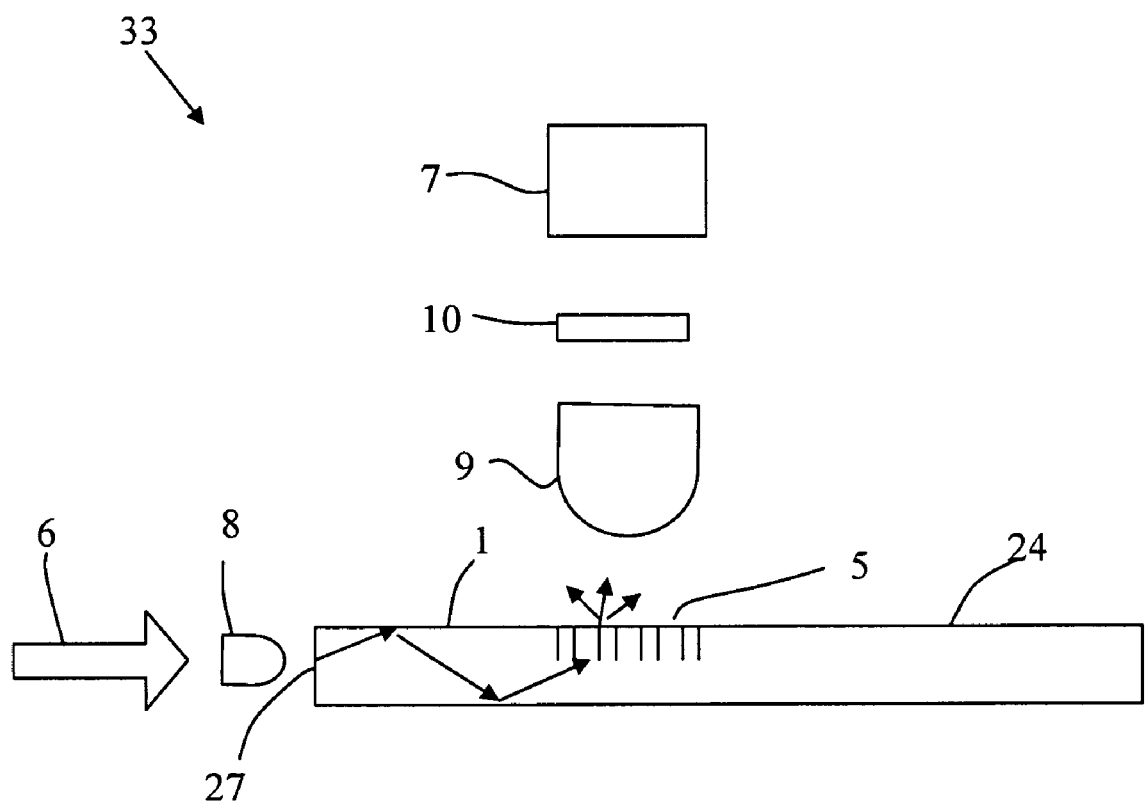
FIG. 6 illustrates an optical reader arranged to illuminate an edge wall of a sample substrate and to detect emitted light from the reaction site surface of the substrate.

FIG. 6 illustrates a first embodiment of an optical reader 33 according to this invention, showing a polymeric sample substrate 1 having a reaction site surface 24, provided with a microstructured reaction site area 5, and an edge wall 27. The optical reader 33 comprises lenses 8, 9 and filter 10, and a light source 6 positioned to inject exciting light rays into the edge 27 of the substrate, the light rays focused on the edge by the lens 8. The configuration of the light source 6, the refractive index of the substrate 1 and the light guiding properties of the lens 8 will influence the light rays, achieving light rays injected in the substrate with a controlled angle of incidence. The injected light rays will be guided in the substrate, e.g. by reflection against the inner walls of the substrate, to propagate towards the reaction site-area 5 and excite fluorophores of the reaction sites. The light emitted from the reaction site area will be focused by the lens 9, filtered by filtering devices 10 and collected by the light detecting device 7, which may be e.g. a PMT.

Figure 7:
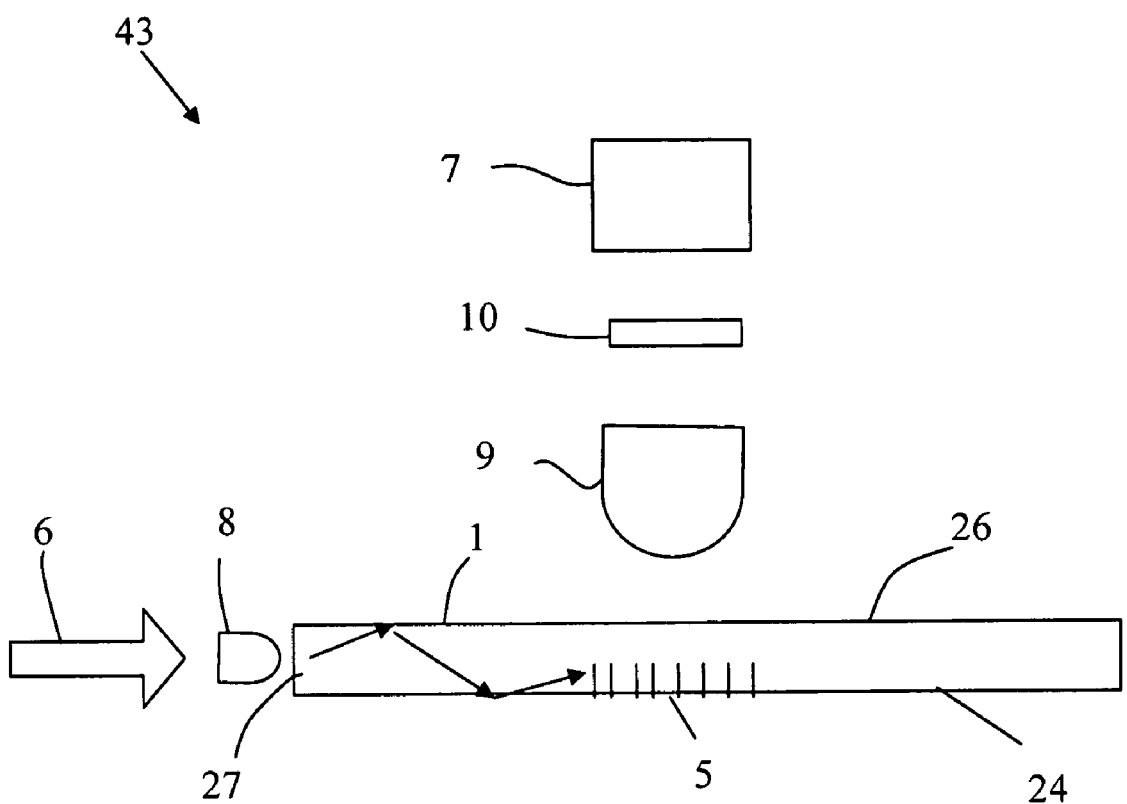
FIG. 7 illustrates an optical reader arranged to illuminate an edge wall of a sample substrate and to detect light emitted from the carrier surface of the substrate.

FIG. 7 illustrates a second embodiment of an optical reader 43 according to this invention, showing a similar set-up as the optical reader 33 shown in FIG. 6. However, according to this second embodiment, the detecting device 7 has a position in relation to the polymeric sample substrate 1 to detect emitted light escaping from the carrier surface 26 of said substrate 1, instead of from the reaction site surface 24. According to this second embodiment, the injected light rays will propagate towards the reaction site-area 5, excite fluorophores of the reaction sites, and the light emitted from the fluorophores will be collected by the lens 9, filtering devices 10 and the light detecting device 7, e.g. a PMT, after transmission through the substrate 1. By means of the detector being positioned to detect emitted light transmitted through the substrate and escaping from the carrier surface 25, an increased fluorescence signal can be detected, thereby increasing the signal-to-noise ratio. This is achieved due to the fact that, under certain circumstances, a larger portion of the fluorescent light from the fluorophores will be emitted inside the substrate than in the air.

Figure 8:
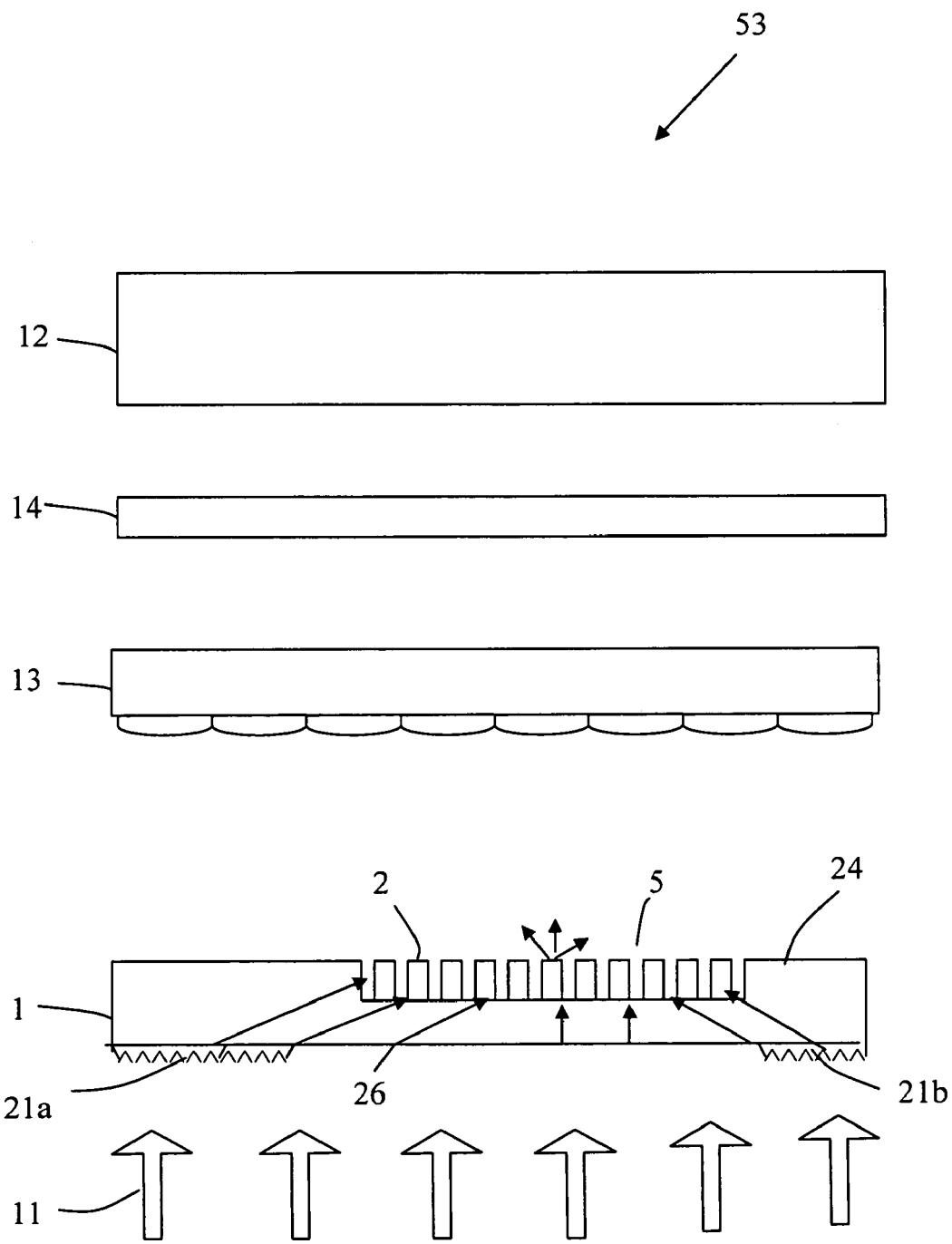
FIG. 8 illustrates an imaging optical reader arranged to illuminate a sample substrate through gratings.

FIG. 8 illustrates a third embodiment of an optical reader 53 according to this invention, being an imaging optical reader of an optical assay arrangement, which comprises a polymeric sample substrate 1 according to a third embodiment of the invention, having a reaction site surface 24 and a carrier surface 26. The reaction site surface comprises a reaction site area 5 provided with micropillars 2, and the carrier surface 26 is provided with gratings 21a, 21b, to control the incidence angle of the exciting light rays. The grating structure is a surface relief that can be of diffractive or refractive nature. The light source 11 is arranged to illuminate substantially the entire area of the carrier surface 26 of the substrate, through said gratings 21a and 21, which are provided adjacent to the edge walls 27a and 27b, and the optical properties of the gratings will influence the incidence angle of the light rays transmitted through said gratings 21a, 21b. Thus, the gratings will refract or diffract the light rays, achieving a controlled incidence angle of the light rays, such that the impinging light rays will be guided within the substrate towards the reaction site area 5. However, the light rays impinging on the surface 26 between said gratings, adjacent to the reaction site area 5, will be substantially parallel to the surface normal, and will be transmitted directly through the substrate to the reaction site area. Thereby, a very efficient illumination of the reaction site area will be accomplished.

Figure 9:
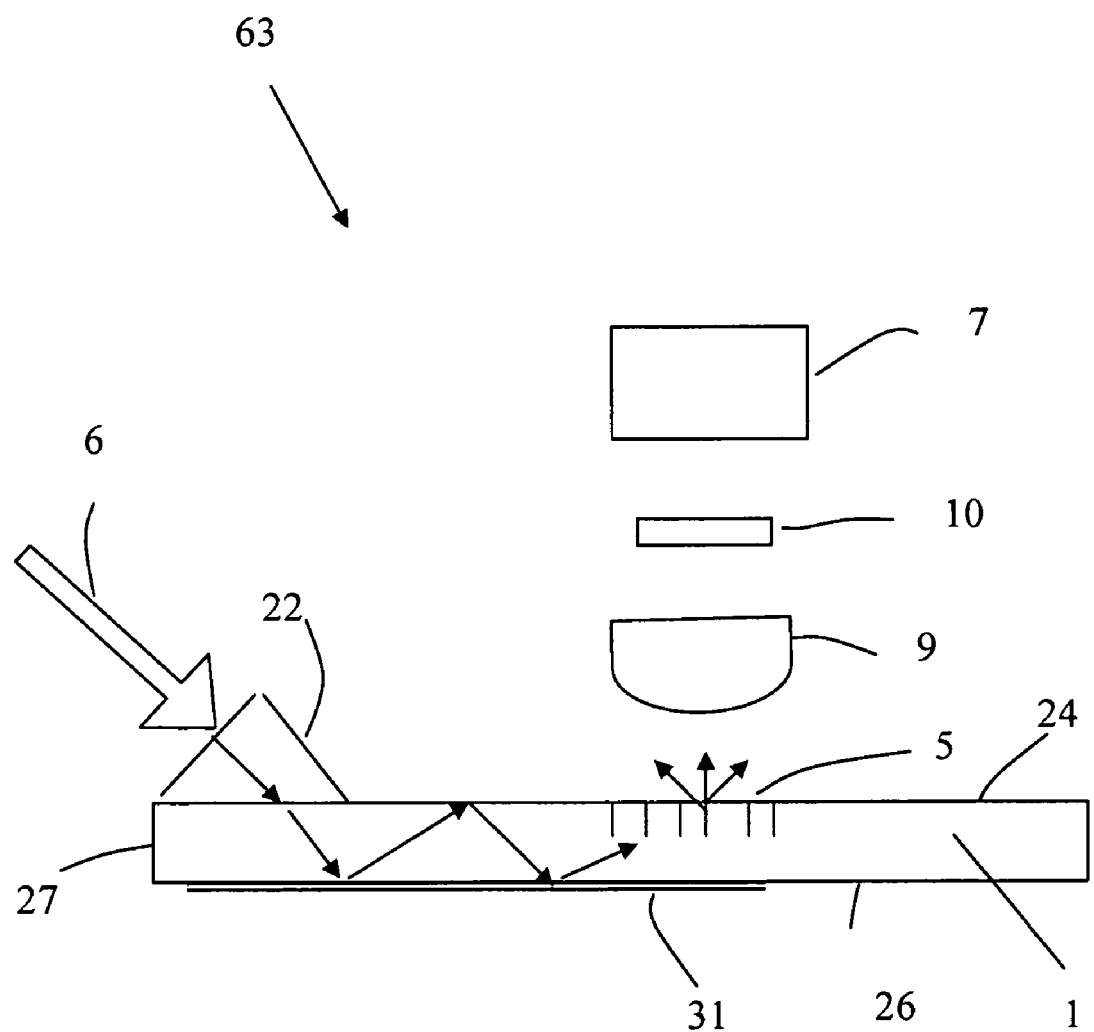
FIG. 9 illustrates an optical reader arranged to illuminate the sample substrate through a prism placed on the reaction site-surface of the substrate and detect light emitted from the reaction site surface.

FIG. 9 illustrates a fourth embodiment of an optical reader 63 according to this invention, in an optical assay arrangement comprising a fourth embodiment of a polymeric sample substrate 1, having a reaction site surface 24, a carrier surface 26 and an edge wall 27, the substrate 1 provided with a microstructured reaction site area 5 on the reaction site surface 24, and an additional layer 31 provided on a part of the carrier surface 26. The light source 6 has a position relative the polymeric sample substrate to illuminate the reaction site surface 24 of the substrate through a light guiding prism 22 placed on the surface 24, adjacent to the edge wall 27. The configuration of the light source 6 and the refracting properties of the prism will provide injected light rays with a controlled incidence angle to be guided by the substrate and of the additional layer 31 in the direction to the reaction site area 5. The light emitted from the reaction-sites will be collected and detected by lens 9, filter 10 and detector 7.

Figure 10:
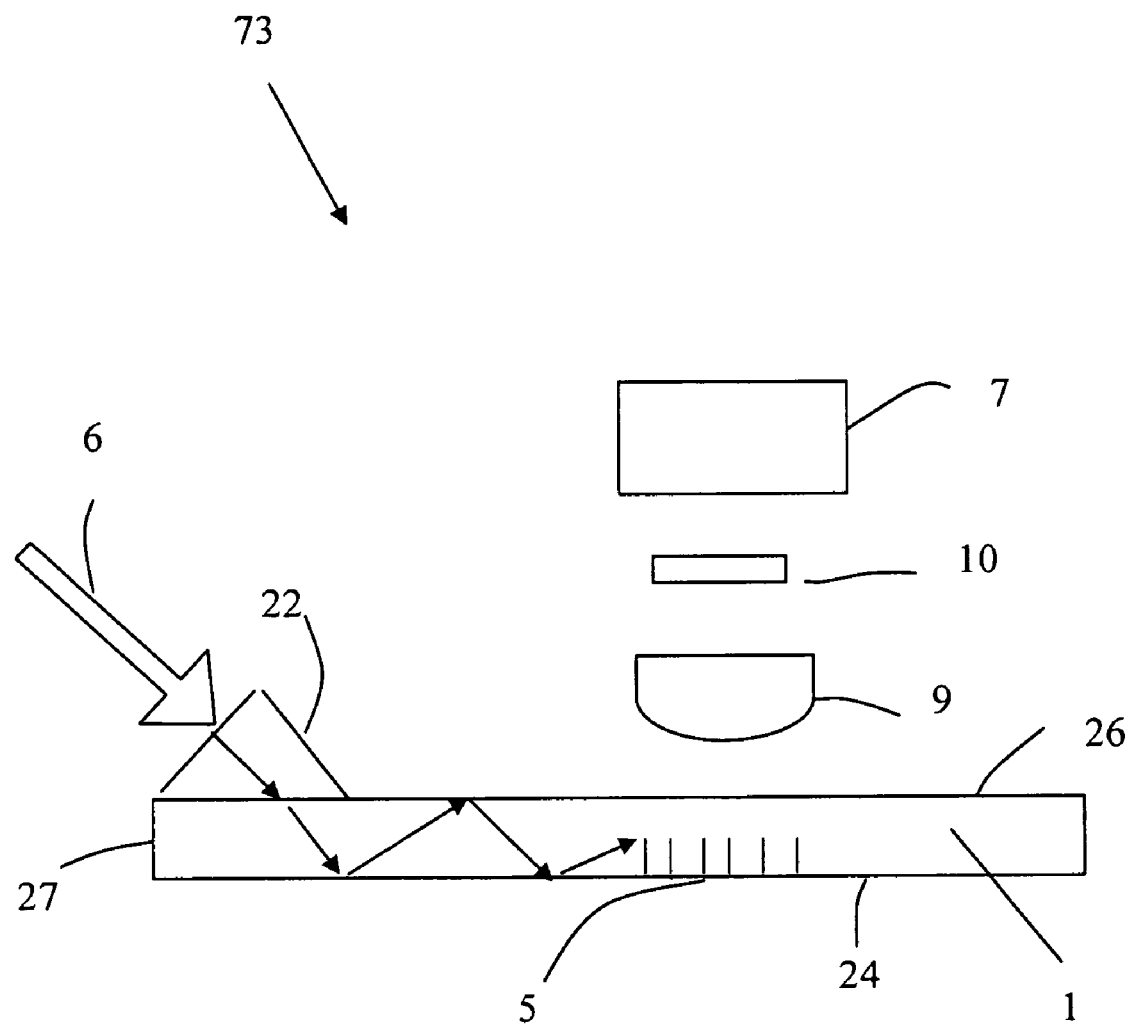
FIG. 10 illustrates an optical reader arranged to illuminate the sample substrate through a prism placed on the carrier surface of the substrate and detect light emitted from the carrier surface of the substrate.

FIG. 10 illustrates a fifth embodiment of an optical reader 73 according to this invention, disclosing of an optical assay arrangement having a similar set-up as in the optical reader 63, according to the fourth embodiment, shown in FIG. 9. However, according to this fifth embodiment, the detecting device 7 has a position relative the polymeric sample substrate 1 to detect emitted light from the carrier surface 26 of said substrate 1, instead of from the reaction site surface 24, and the substrate is not provided with any semi-reflecting layer. Further, the light source 6 has a position relative the polymeric sample substrate 1 to illuminate the carrier surface 26 of the substrate (instead of the reaction site surface 24), through a light guiding prism 22 placed on the surface 26, adjacent to the edge wall 27. The configuration of the light source 6 and the refracting properties of the prism will provide injected light rays with a controlled incidence angle to be guided by the substrate to propagate towards the reaction site-area 5, exciting fluorophores provided on the reaction sites. Since most of the fluorescent light is emitted inside the substrate, and not in the air, a substantial fraction of the light emitted from the fluorophores will be transmitted through the substrate 1, collected by the lens 9, filtering devices 10 and the light detecting device 7, e.g. a PMT.

Figure 11:
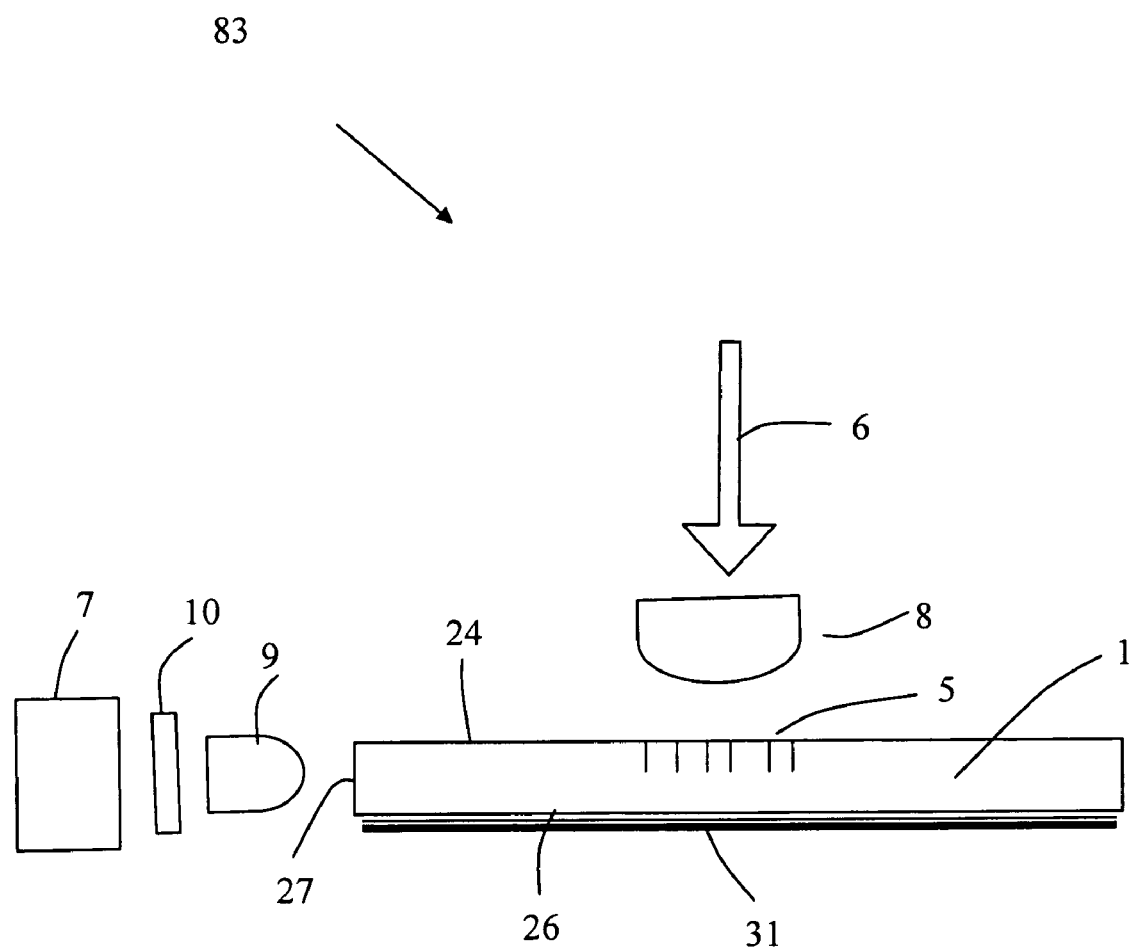
FIG. 11 illustrates an optical reader arranged to illuminate the reaction site surface of a sample substrate and detect light emitted from an edge wall of the substrate.

FIG. 11 illustrates a sixth embodiment of an optical reader 83 according to this invention, and a fifth embodiment of a polymeric sample substrate 1, having a reaction site surface 24 provided with a microstructured reaction site area 5, and the entire carrier surface 26 covered with an additional layer 31. The optical reader 83 comprises a light source 6 positioned relative the polymeric sample substrate 1 to inject exciting light rays directly into the reaction site area 5, and a detecting device 7 positioned relative the polymeric sample substrate 1 to receive emitted fluorescent light escaping from the edge wall 27. The exciting light rays from the light source impinges on the surface 24 guided by the lens 8, with a direction approximately corresponding to the normal of the surface 24, i.e. with a relatively small incidence angle, such as e.g. less than 10☐ The light rays will excite the fluorophores in the reaction sites, and a large fraction of the emitted fluorescent light will be transmitted in various, different directions within the substrate. The emitted light will be reflected from the inner surfaces of the substrate, and of the additional, semi-reflecting layer 31 provided on the carrier surface 26 of the substrate, causing a fraction of the emitted fluorescent to be guided in the direction of the edge wall 27, to be collected by the detecting device 7, which is arranged to receive light escaping from the edge wall 27, through a lens 9 and a filter 10.

According to a sixth embodiment of a polymeric sample substrate according to this invention, a light guiding prism 22 is attached on a surface of the substrate.

The six embodiments of optical readers according to this invention, shown in FIGS. 6-11, show exemplary configurations of the position of the light source 6 and the detector device 7, in relation to the position of a polymeric sample substrate 1. However, according to other embodiments of this invention, the light source 6 can be positioned to inject exciting light rays into any of the two surfaces 24, 26, or into any edge wall 27 of a substrate. Similarly, according to still further embodiments of this invention, the detecting device 6 can be positioned to detect fluorescent or phosphorescent light escaping from any of the two surfaces 24 or 26, or from any of the edge walls 27.

Additionally, the light source 6 and detector device 7 can either be positioned to inject exciting light rays and to detect emitted light from the same surface or edge wall, or from different surfaces of edge walls.

Thus, the invention is not restricted to the described embodiments in the figures, but may be varied freely within the scope of the appended claims.

The invention claimed is:

1. An optical reader for an optical assay arrangement, comprising:
   a polymeric sample substrate comprising:
      a reaction-site surface comprising:
         protruding microstructures; and
         at least one reaction-site area;
   a light source; and
   a detector device,
   wherein the light source is arranged to inject exciting light rays into the polymeric sample substrate with a controlled angle of incidence such that the protruding microstructures guide the exciting light rays in the direction of the reaction-site area, and the detector device detects light emitted from the at least one reaction-site area.

2. The optical reader of claim 1, further comprising an additional layer with selected optical properties, wherein the polymeric sample substrate is at least partly covered with the additional layer.

3. The optical reader of claim 2, wherein the additional layer is applied as an optically wetting layer arranged to increase an angle of refraction of the exciting light rays.

4. The optical reader of claim 2, wherein the additional layer at least partly covers the protruding microstructures.

5. The optical reader of claim 2, further comprising a carrier surface of the polymeric sample substrate, wherein the additional layer at least partly covers the carrier surface.

6. The optical reader of claim 2, wherein the additional layer is arranged to absorb selected optical wavelengths.

7. The optical reader of claim 2, wherein the additional layer consists of a tape of a suitable material attached to the polymeric sample substrate.

8. The optical reader of claim 1, further comprising a light guiding device, wherein the light source is adapted to illuminate the polymeric sample substrate through the light guiding device arranged to control an angle of refraction of the exciting light rays inside the polymeric sample substrate.

9. The optical reader of claim 8, further comprising a carrier surface of the polymeric sample substrate, wherein the light guiding device comprises a prism placed on the reaction-site surface or the carrier surface of the polymeric sample substrate.

10. The optical reader of claim 8, further comprising a carrier surface of the polymeric sample substrate, wherein the light guiding device comprises a diffractive or refractive grating provided on the reaction-site surface or the carrier surface of the polymeric sample substrate.

11. The optical reader of claim 1, wherein the light source has a position relative to the polymeric sample substrate to illuminate the reaction-site surface of the polymeric sample substrate.

12. The optical reader of claim 1, further comprising a carrier surface of the polymeric sample substrate, wherein the light source has a position relative to the polymeric sample substrate to illuminate the carrier surface.

13. The optical reader of claim 1, further comprising an edge wall of the polymeric sample substrate, wherein the light source has a position relative to the polymeric sample substrate to illuminate the edge wall of the polymeric sample substrate.

14. The optical reader of claim 1, wherein an arrangement of the light source causes an angle of refraction to exceed a critical angle for total internal reflection to occur within the polymeric sample substrate.

15. The optical reader of claim 1, wherein the detector device has a position relative to the polymeric sample substrate to collect fluorescent or phosphorescent light emitted from a the reaction-site area of the substrate, the emitted light guided in the direction of the detector device by the protruding microstructures of the polymeric sample substrate.

16. The optical reader of claim 1, further comprising a carrier surface of the polymeric sample substrate, wherein the detector device has a position relative to the polymeric sample substrate to receive emitted fluorescent or phosphorescent light escaping from the carrier surface.

17. The optical reader of claim 1, further comprising an edge wall of the polymeric sample substrate, wherein the detector device has a position relative to the polymeric sample substrate to receive emitted fluorescent or phosphorescent light escaping from the edge wall.

18. The optical reader of claim 1, further comprising a carrier surface and an edge wall of the polymeric sample substrate, wherein the light source has a position relative to the polymeric sample substrate to illuminate the reaction-site surface carrier surface, or edge wall, and the detector device has a position relative to the polymeric sample substrate to receive emitted fluorescent or phosphorescent light escaping from the reaction-site surface, carrier surface, or edge wall.

19. The optical reader of claim 1, further comprising a carrier surface and an edge wall of the polymeric sample substrate, wherein the light source has a position relative to the polymeric sample substrate to illuminate the reaction-site surface, carrier surface, or edge wall, and the detector device has a position relative to the polymeric sample substrate to receive emitted fluorescent or phosphorescent light escaping from the reaction-site surface, carrier surface, or edge wall.

20. The optical reader of claim 1, wherein the optical reader is arranged as an imaging optical reader.

21. The optical reader of claim 1, wherein the optical reader is arranged as a scanning optical reader.

22. An optical assay arrangement comprising an optical reader according to claim 1, and the optical reader further comprising an additional layer with selected optical properties, a carrier surface, and a light guiding device, wherein the polymeric sample substrate is at least partly covered with the additional layer; the protruding microstructures and the additional layer guide exciting light rays in the direction of the reaction-site area; and the light guiding device is attached on the reaction-site surface or carrier surface for controlling an angle of incidence of the exciting light rays illuminating the polymeric sample substrate.

23. A polymeric sample substrate for an optical assay arrangement comprising:
a reaction-site surface comprising:
protruding microstructures; and
at least one reaction-site area;
an additional layer with selected optical properties;
a carrier surface; and
a light guiding device,
wherein the protruding microstructures guide exciting light rays from a light source in the direction of the reaction-site area, and the light guiding device is attached to the reaction-site surface or the carrier surface of the polymeric sample substrate to control an angle of incidence of the exciting light rays.

24. The polymeric sample substrate of claim 23, wherein the additional layer at least partly covers the protruding microstructures .

25. The polymeric sample substrate of claim 23, wherein the additional layer at least partly covers the carrier surface.

26. The polymeric sample substrate of claim 23, wherein the additional layer is applied as an optically wetting layer arranged to increase an angle of refraction of the exciting light rays.

27. The polymeric sample substrate of claim 23, wherein the additional layer is arranged to absorb selected optical wavelengths.

28. The polymeric sample substrate of claim 23, wherein the additional layer consists of a tape of a suitable material attached to the substrate.

29. The polymeric sample substrate of claim 23, wherein the light guiding device comprises a prism.

30. The polymeric sample substrate of claim 23, wherein the light guiding device comprises a diffractive or refractive grating.

* * * * *